(12) United States Patent
Scherrer et al.

(10) Patent No.: US 11,213,335 B2
(45) Date of Patent: Jan. 4, 2022

(54) MODULAR RETAINING SCREWDRIVER

(71) Applicant: DEPUY SYNTHES PRODUCTS, INC., Raynham, MA (US)

(72) Inventors: Simon Scherrer, Zurich (CH); Gregor Spreiter, Zuchwil (CH); Henri Défossez, Neuchatel (CH); Simon Wampfler, Lohn-Ammannsegg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 16/851,090

(22) Filed: Apr. 16, 2020

(65) Prior Publication Data

US 2021/0322078 A1  Oct. 21, 2021

(51) Int. Cl.
| | |
|---|---|
| *A61B 17/04* | (2006.01) |
| *A61B 17/86* | (2006.01) |
| *A61F 2/08* | (2006.01) |
| *A61B 17/88* | (2006.01) |
| *A61B 17/00* | (2006.01) |
| *A61B 17/56* | (2006.01) |

(52) U.S. Cl.
CPC ...... *A61B 17/8888* (2013.01); *A61B 17/8615* (2013.01); *A61B 2017/0042* (2013.01); *A61B 2017/00477* (2013.01); *A61B 2017/564* (2013.01)

(58) Field of Classification Search
CPC combination set(s) only.
See application file for complete search history.

(56) References Cited

U.S. PATENT DOCUMENTS 8,591,515 B2 * 11/2013 Jackson ............. A61B 17/7082
606/86 A

* cited by examiner

*Primary Examiner* — Sameh R Boles
(74) *Attorney, Agent, or Firm* — Fay Kaplun & Marcin, LLP (57) ABSTRACT

A modular system for treating a bone includes a main body including a channel extending therethrough. A distal end includes a driving feature sized and shaped to engage a corresponding driving structure of one of first and second bone screws. The system also includes an inner shaft sized and shaped to be inserted into the channel and including a distal end including a retaining feature for engaging a corresponding retaining structure extending within a recess at a proximal end of the first screw. Furthermore, the system includes an outer shaft extending longitudinally and including a channel extending therethrough. The channel of the outer shaft is sized and shaped to slidably receive the main body therein and including a retaining feature extending along a distal end thereof. The retaining feature of the outer shaft engages a retaining structure extending along an exterior surface of the second screw.

11 Claims, 5 Drawing Sheets

MODULAR RETAINING SCREWDRIVER

BACKGROUND

Bone screws may be used to fix bone fixation devices such as, for example, intramedullary nails and/or bone plates, relative to the bone. Bone screws are inserted into the bone using a driving device such as a screwdriver. In some cases, a bone screw may become disengaged from the screw during driving of the screw into the bone, which may result in loss of the bone screw and/or difficulty inserting the bone screw.

SUMMARY

The present disclosure relates to a modular system for treating a bone. The system includes a main body including an elongated member extending from a proximal end to a distal end and including a channel extending longitudinally therethrough, the proximal end attached to a handle member and the distal end including a driving feature sized and shaped to engage a corresponding driving structure of one of a first bone screw and a second bone screw; an inner shaft including a longitudinal element sized and shaped to be inserted through the channel of the elongated member of the main body, the longitudinal element extending from a proximal end to a distal end including a retaining feature for engaging a corresponding interior retaining structure extending within a recess at a proximal end of the first bone screw; and an outer shaft extending longitudinally from a proximal end to a distal end and including a channel extending therethrough, the channel sized and shaped to slidably receive the elongated member of the main body therein and including a retaining feature extending along the distal end thereof, the retaining feature of the outer shaft configured to engage an exterior retaining structure extending along an exterior surface of the second bone screw, wherein the main body is selectively assemblable with one of the inner and outer shaft to drive one of the first and second bone screws into a bone.

In an embodiment, the retaining feature of the inner shaft includes a threading extending along the distal end thereof.

In an embodiment, the inner shaft includes a knob attached to the proximal end of the longitudinal element, the knob extending proximally of the handle member of the main body when the inner shaft is assembled with the main body.

In an embodiment, the knob includes a plurality of grooves along a radially outermost surface thereof to facilitate gripping of the knob.

In an embodiment, each of the plurality of grooves is asymmetrical about a central axis extending through a center of the knob and a midpoint between a first end and a second end of each groove.

In an embodiment, each of the plurality of grooves is configured as a substantially arcuate recess so that a first portion of the arcuate recess extending between the first end and the midpoint has a larger radius of curvature than a second portion of the arcuate recess extending between the second end and the midpoint.

In an embodiment, the retaining feature of the outer shaft includes a threading extending along an interior surface of the channel at the distal end of the outer shaft.

In an embodiment, the outer shaft include a locking member including a tab biased into the channel thereof and the elongated member includes a corresponding locking groove extending about a portion thereof so that, when the elongated member is inserted into the channel of the outer shaft, the tab of the locking member is pushed out of the channel until the locking groove is positioned adjacent the tab and the tab is permitted to revert to its biased configuration to be received within the locking groove.

In an embodiment, the driving structure of the first and second bone screws is configured as a first recess extending into the proximal end thereof, the first recess sized and shaped to correspond to the driving feature of the main body.

In an embodiment, the first and second bone screw further includes a second recess extending distally from the first recess, the retaining structure of the first and second bone screw including a threading extending along the second recess.

In an embodiment, the second bone screw includes a threading extending about an entire length thereof.

The present disclosure also relates to a method for treating a bone. The method includes selecting one of a first bone screw and a second bone screw for implantation into a bone, the first bone screw including a retaining structure extending along an interior surface thereof defined via a recess extending distally into a proximal end thereof, the second bone screw including a retaining structure extending along an exterior surface along a proximal portion thereof, and assembling one of an inner shaft and an outer shaft with a main body of a modular screwdriver system to form a retaining screwdriver based on a selected one of the first and second bone screws, the main body including an elongated member extending from a proximal end to a distal end and including a channel extending longitudinally therethrough, the distal end including a driving feature sized and shaped to correspond to the driving structure of one of a first bone screw and a second bone screw, the inner shaft including a retaining feature for engaging the retaining structure of the first bone screw, and the outer shaft including a retaining feature configured to engage the retaining structure of the second bone screw.

In an embodiment, of the inner shaft and the outer shaft is assembled with the main body to permit a rotation of the assembled one of the inner shaft and the outer shaft relative to the elongated member of the main body.

In an embodiment, assembling the inner shaft within the main body includes inserting a longitudinal element of the inner shaft through the channel of the elongated member of the main body so that a distal end of the longitudinal member, which includes the retaining feature of the inner shaft, extends distally past the driving feature of the main body.

In an embodiment, assembling the outer shaft within the main body includes inserting the elongated member of the main body through a channel of the outer shaft.

In an embodiment, when the elongated member is inserted into a desired position within the outer shaft, a locking member of the outer shaft reverts to a biased configuration to be received within a corresponding locking groove extending about a periphery of the elongated member.

In an embodiment, the method further includes coupling the assembled retaining screwdriver to one of the first and second bone screws.

In an embodiment, coupling the assembled retaining screwdriver to the first bone screw includes threadedly engaging the retaining feature of the inner shaft with the retaining structure of the first bone screw and inserting the driving feature of the main body into the driving structure of the first bone screw.

In an embodiment, coupling the retaining feature of the inner shaft to the retaining structure of the first bone screw includes rotating the inner shaft relative to the first bone screw in a first direction via a knob attached to a proximal end of the longitudinal member of the inner shaft, the knob extending proximally of a handle member attached to a proximal end of the elongated member of the main body.

In an embodiment, the knob includes a plurality of grooves along a radially outermost surface thereof to facilitate gripping of the knob, each of the plurality of grooves configured as a substantially arcuate recess so that a first portion of the arcuate recess extending between the first end and the midpoint has a larger radius of curvature than a second portion of the arcuate recess extending between the second end and the midpoint, a user gripping the first portion of the knob when rotating the inner shaft in the first direction.

In an embodiment, the inner shaft is disengaged from the first bone screw by rotating the inner shaft in a second direction opposite the first direction relative to the main body, the user gripping the second portion of the knob when rotating the inner shaft in the second direction.

In an embodiment, coupling the assembled retaining screwdriver to the second bone screw includes threadedly receiving the retaining structure of the second bone screw within a distal end of the outer shaft and inserting the driving feature of the main body into the driving structure of the first bone screw so that, as the main body is rotated relative to the outer shaft to drive the second bone screw into bone, the retaining structure of the second bone screw is unthreaded from the retaining feature of the outer shaft.

BRIEF DESCRIPTION

DETAILED DESCRIPTION

The present disclosure may be understood with reference to the following description and the appended drawings, wherein like elements are referred to with the same reference numerals. The present embodiments relate to the treatment of bone and, in particular, relates to a modular screwdriver system including features for engaging and driving a variety of different types of bone screws. Exemplary embodiments describe a modular retaining screwdriver system which combines instrumentation for driving different types of retaining bone screws. Retaining bone screws include retaining features configured to engage a screwdriver so that the bone screw is prevented from disengaging the screwdriver during insertion of the bone screw into the bone, providing easier and faster insertion of the bone screws.

The exemplary modular screwdriver system comprising both an inner shaft and an outer shaft that may be selectively assembled with a main longitudinal body to drive either a bone screw in which retention features extend within an interior of the bone screw head or a bone screw in which retention features extend along an exterior of a bone screw head, respectively. The combined instrumentation may reduce costs and save space on a surgical tray. It will be understood by those of skill in the art that although the exemplary embodiments may be shown and described with respect to locking bone screws for an intramedullary nail, the screwdriver system of the present disclosure may be utilized for engaging and driving any of a variety of bone screws in any of a number of different types of bone fixation systems. For example, the screwdriver system of the present invention may also be used to place an isolated single screw, a screw for fixation of a bone plate or a combination thereof.

As shown in FIGS. 1-8, a modular retaining screwdriver system 100 according to an exemplary embodiment of the present disclosure comprises a main body 102 to which either an inner shaft 104 or an outer shaft 106 may be selectively assembled to engage and drive a bone screw such as, for example, a bone screw. One possible bone screw is shown as a first bone screw 108 which includes a retaining structure 130 extending along an interior of a head portion 120 thereof. Alternatively, a second bone screw 110 may be engaged which includes a retaining structure 132 extending along an exterior of a head portion 124 thereof. The main body 102 further comprises an elongated member 112 for engaging one of the inner and outer shafts 104, 106 and a handle portion 114.

Figure 1:
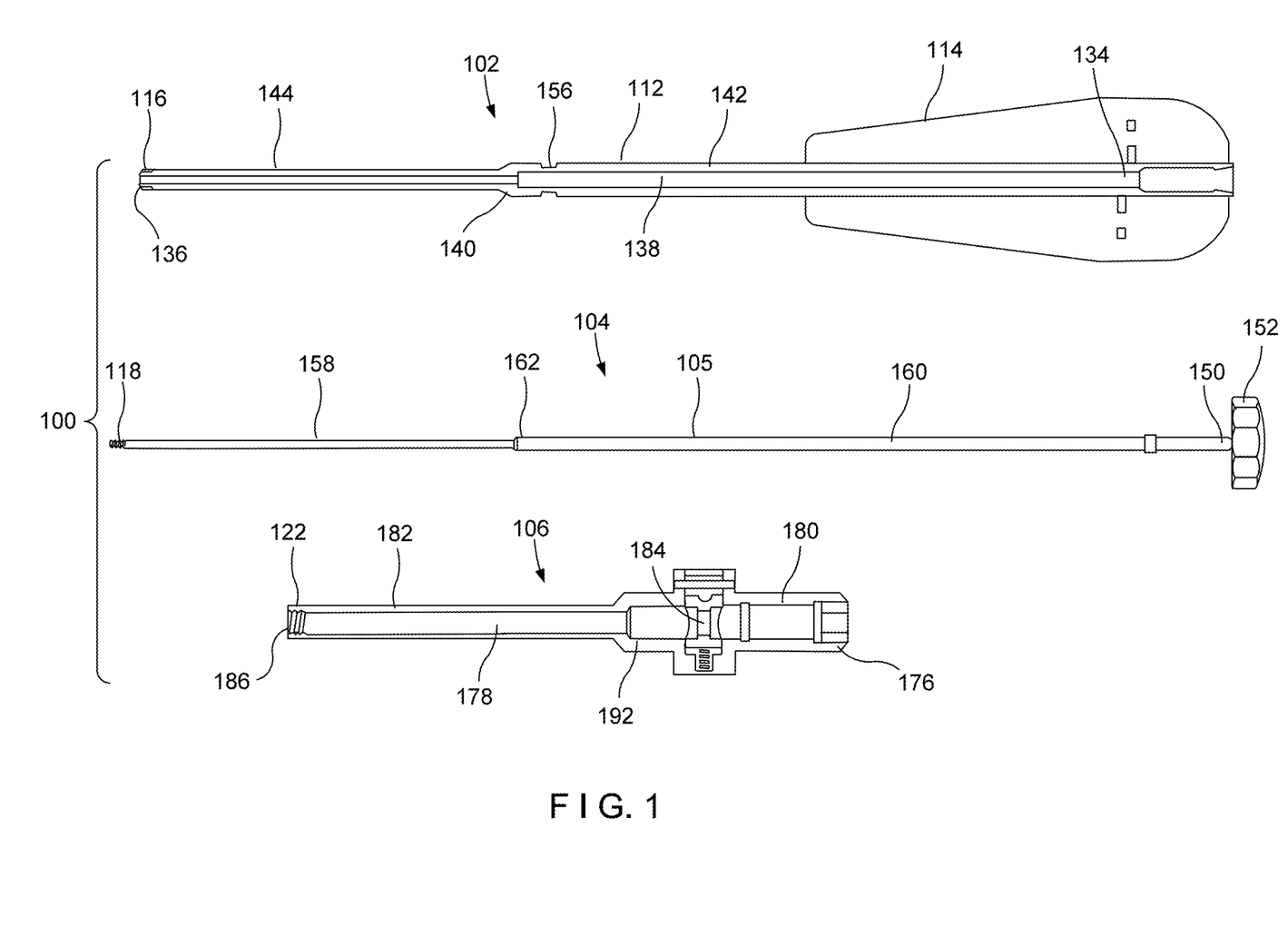
FIG. 1 shows a longitudinal side view of a system according to an exemplary embodiment of the present disclosure.
Figures 2, 3, 4, 5:
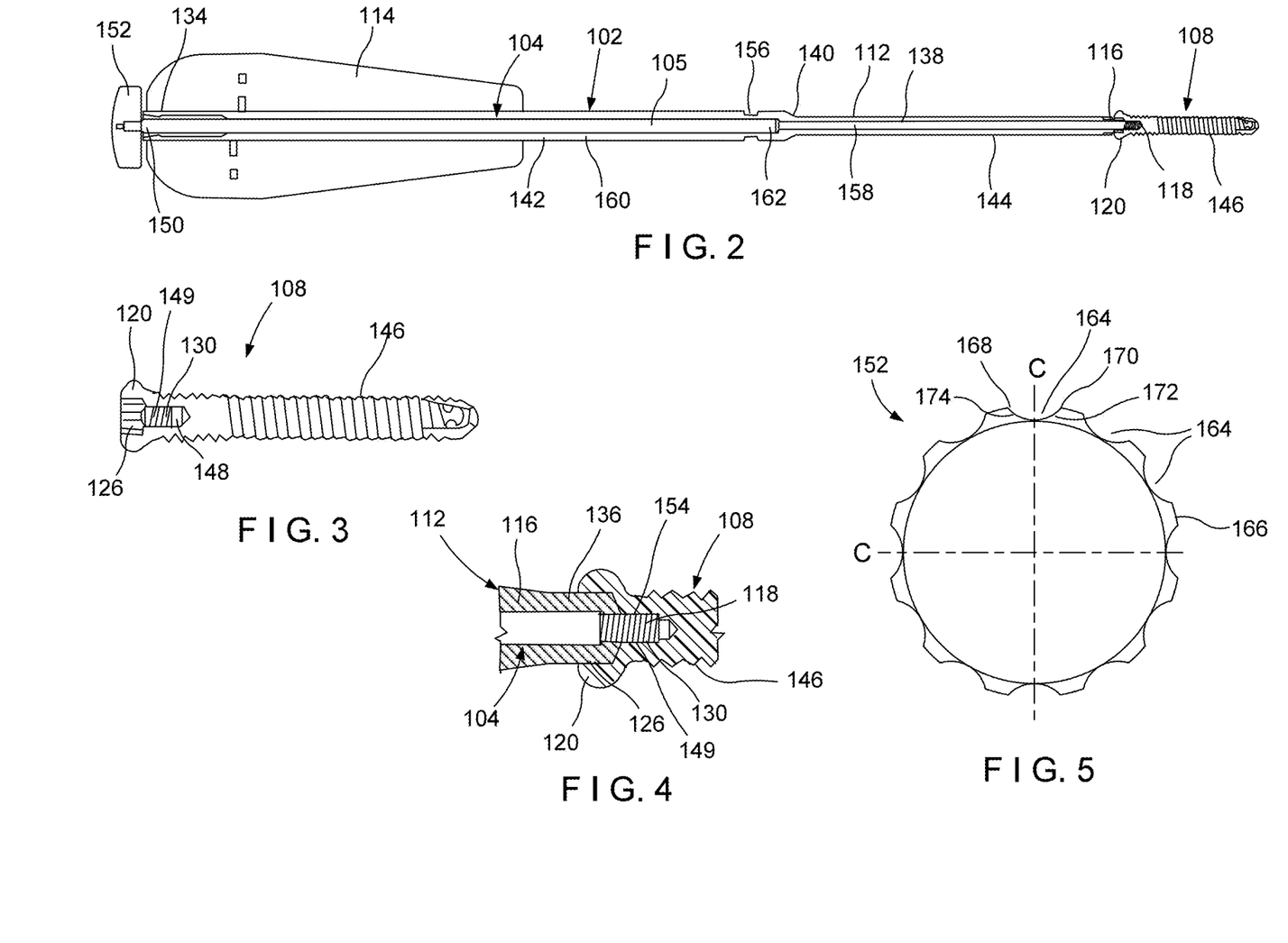
FIG. 2 shows a longitudinal cross-sectional view of a first assembly of the system of FIG. 1, in which a main body is assembled with an inner shaft.
FIG. 3 shows a partial cross-sectional view of a first bone screw according to the system of FIG. 1.
FIG. 4 shows an enlarged longitudinal cross-sectional view of an engagement of the main body and inner shaft with a bone screw, as shown in FIG. 2.
FIG. 5 shows a lateral side view of a knob of the inner shaft according to the system of FIG. 1.
Figure 6:
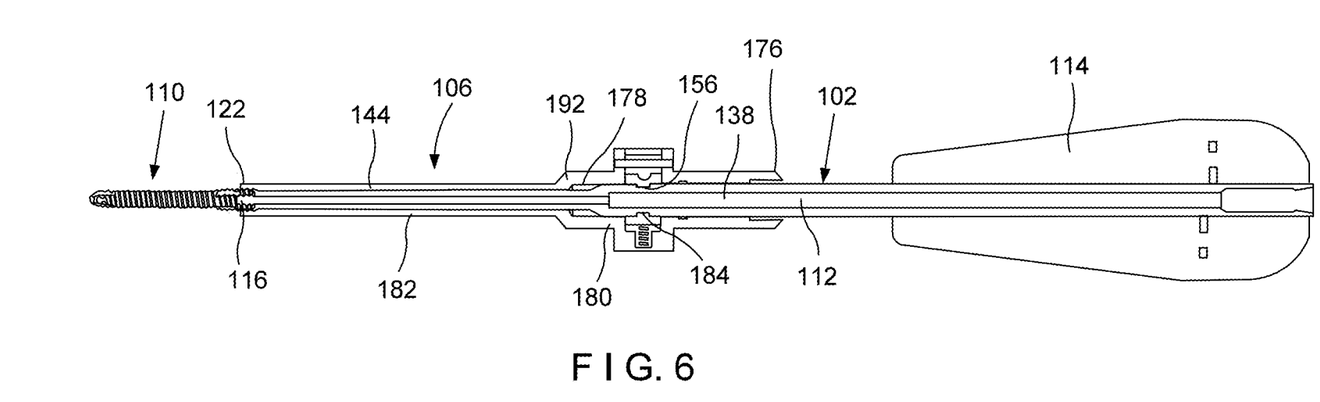
FIG. 6 shows a longitudinal cross-sectional view of a second assembly of the system of FIG. 1 in which the main body assembled with an outer shaft according to the system of FIG. 1.

A distal end 116 of the elongated member 112 is configured to engage, for example, correspondingly sized and shaped driving structures 126, 128 of the bone screws 108, 110 so that rotation of the elongated member 112 via the handle portion 114 rotatably drives the first and second bone screws 108, 110 into or out of a bone, depending on the direction of rotation. A distal end 118 of the inner shaft 104 is configured to engage the retaining structure 130 of the first screw 108 so that, when the inner shaft 104 and the main body 102 are assembled with one another, the inner shaft 104 may engage and retain the first screw 108 while the first screw 108 is being driven into or out of the hone. A distal end 122 of the outer shaft 106 is configured to engage a retaining structure 132 of the second bone screw 110 so that, when the outer shaft 106 is assembled with the main body 102, the outer shaft 106 may engage and retain the second screw 110 while the second screw 110 is being driven into or out of the bone.

The main body 102 includes the elongated member 112 extending along a longitudinal axis from a proximal end 134 to the distal end 116. The handle portion 114 is attached to the proximal end 134 so that the handle portion 114 may be gripped by a user (e.g., surgeon). The distal end 116 includes a driving feature 136 configured to engage a correspondingly sized and shaped driving structure of a bone screw such as, for example, the driving structures 126, 128 of the first and second bone screws 108, 110, respectively, so that rotation of the handle portion 114 about the longitudinal axis of the elongated member 112 rotatably drives the first and second bone screws 108, 110 into or out of the bone. In one embodiment, the driving feature 136 includes a hex or star shaped structure configured to be inserted into a correspondingly sized and shaped recess of the driving structures 126, 128. It will be understood by those of skill in the art, however, that the driving feature 136 may have any of a variety of sizes and shapes so long as the driving feature 136 is configured to be non-rotationally received within the driving structures 126, 128 of the first and second bone screw 108, 110 so that rotation of the main body 102 rotatably drives first and second bone screws 108, 110.

The elongated member 112 includes a proximal portion 142 and a distal portion 144 connected to one another via a shoulder 140. A channel 138 extending through both the proximal and distal portions 142, 144 from the proximal end 134 to the distal end 116 and is sized and shaped to receive the inner shaft 104 therein. The proximal portion 142 has both a larger inner and outer diameter than the distal portion 144 so that the shoulder 140 provides a transition therebetween. Thus, a portion of the channel 138 extending through the distal portion 144 has a smaller diameter than a portion of the channel 138 extending through the proximal portion 142. As will be described in further detail below, an interior surface of the shoulder 140 is configured to about a portion of the inner shaft 104 that is inserted into the channel 138 to define a distal-most position of the inner shaft 104 relative to the main body 102.

In one embodiment, the proximal portion 142 includes a locking recess 156 extending thereabout. The recess 156 is sized and shaped to receive a locking structure 184 of the outer shaft 106 therein when the outer shaft 106 is mounted over the elongated member 112 of the main body 102, in a desired configuration. The recess 156 may be configured as, for example, a circular groove extending about the proximal portion 142 at a point therealong. Although the locking recess 156 is shown and described as extending about the proximal portion 142, it will be understood by those of skill in the art that, in an alternate embodiment, the locking recess 156 extends about the distal portion 144.

As described above, the inner shaft 104 is configured to be assembled with the main body 102 to retain the first bone screw 108, as the first bone screw 108 is being driven into or out of the bone. The first bone screw 108 includes the retaining structure 130 along the interior of the head portion 120. According to one example, the first bone screw 108 is a standard bone screw including a smooth head portion 120 for abutting an exterior surface of a bone and a threaded shaft portion 146 configured to be driven into the bone to pass through, for example, a locking hole of an intramedullary nail or other implant. The driving structure 126 is sized and shaped to correspond to the driving feature 136 of the elongated member 112 and, in one embodiment, includes a hex or star shaped recess extending into the head portion 120.

The retaining structure 130 extends distally from the driving structure 126, further distally into the head portion 120. In one embodiment, the retaining structure 130 includes a recess 148 extending from the driving structure 136, the recess 148 including a threading 149 along a surface thereof. Although the retaining structure 130 is shown and described as a threaded recess, it will be understood by those of skill in the art that the retaining structure 130 may have any of a variety of structures engaging the head portion 120 so long as the retaining structure 130 is configured to engage the inner shaft 104 while the first bone screw 108 is being rotatably driven.

The inner shaft 104 includes a longitudinal element 105 extending from a proximal end 150 to the distal end 118 and a knob 152 attached to the proximal end 150. The proximal end 150 of the longitudinal element 105 may also include a retaining feature therealong configured to secure the inner shaft 104 to the main body 102 such that the inner shaft 104 is prevented from becoming unintendedly disassembled from the main body 102 during handling. The distal end 118 includes a retaining feature 154 for engaging the retaining structure 130 of the first bone screw 108. In one embodiment, the retaining feature 154 is configured as a threading along the distal end 118 configured to engage threading of the threaded recess 148 of the retaining structure 130 of the first bone screw 130. It will be understood by those of skill in the art, however, that the retaining feature 154 of the inner shaft 104 may have any of a variety of configurations so long as the retaining feature 154 corresponds to a retaining structure 130 of the first bone screw 108.

The longitudinal element 105 of the inner shaft 104 includes a distal portion 158 sized and shaped to correspond the distal portion 144 of the channel 138 of the elongated member 112 of the main body 102 and a proximal portion 160 sized and shaped to correspond to the proximal portion 142 of the channel 138. In other words, the proximal portion 160 has a larger diameter than the distal portion 158. A distal end 162 of the proximal portion 160 is configured to abut the shoulder 140 of the channel 138 when inserted therethrough. Lengths of the proximal and distal portions 160, 158 are selected so that, when the longitudinal element 105 of the inner shaft 104 is inserted into the channel 138 with the distal end 162 of the distal portion 158 abutting the shoulder 140, the distal end 118 of the inner shaft 104 extends distally from the distal end 116 of the elongated member 112 by a distance corresponding to a depth of the recess 148 of the retaining structure 130 of the first bone screw 108.

When the inner shaft 104 is assembled with the main body 102, the longitudinal element 105 is inserted through the channel 138 of the elongated member 112 so that the knob 152 of the inner shaft 104 extends proximally of the handle member 114. In one embodiment, the knob 152 is sized, shaped and configured to facilitate rotation of the knob 152, and thereby the longitudinal element 105 extending distally therefrom, about a longitudinal axis of the longitudinal element 105 so that the threading of the retaining feature 154 along the distal end 118 may engage the threading 149 of the retaining structure 130 of the first bone screw 108. For example, the knob 152 may be rotated in a first direction (e.g., clockwise) about the longitudinal axis of the longitudinal element 105 to engage the retaining feature 154 of the inner shaft 104 with the retaining structure 130 of the first screw 108.

To disengage the retaining feature 154 from the retaining structure 130, the knob 152 may be rotated in a second direction (e.g., counter-clockwise) opposite the first direction. The knob 152 may include a plurality of grooves 164 about a periphery thereof to facilitate gripping of the knob 152 during rotation thereof. In one embodiment, the grooves 164 extend along a radially outer-most surface 166 of the knob 152. Each of the grooves 164 may be configured as a substantially arcuate recess extending into the radially outermost surface 166 so that each groove 164 is substantially symmetrical about a central axis C extending through a center of the knob 152 and a point midway between a first end 168 and a second end 170 of each of the grooves 164. In another embodiment, as shown in FIG. 5, however, each of the grooves 164 is asymmetrical about the central axis C, a first portion 172 of the groove 164 along a first side of the central axis having a larger radius of curvature than a second portion 174 of the groove 164 on a second side of the central axis C.

The first portion 172 of the groove 164 extends along a side of the groove 164 on which the user exerts force when rotating the knob 152 in the first (e.g., clockwise) direction, while the second portion 174 of the groove 164 extends along a side of the groove 164 on which the user exerts a force when rotating the knob 152 in the second (e.g., counter-clockwise) direction. In other words, an angle of a surface area of the groove 164 is configured so that a resulting force vector is moved toward a radial direction to facilitate, for example, a loosening of the knob 152.

Figure 7:
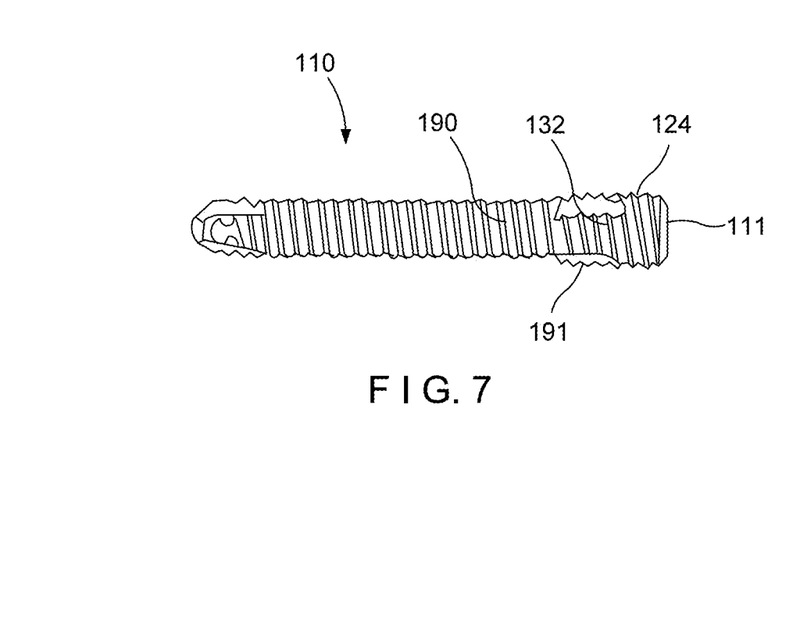
FIG. 7 shows a longitudinal side view of a second bone screws according to the system of FIG. 1.

The outer shaft 106 may be assembled with the main body 102 to retain the second bone screw 110 while the second bone screw 110 is being inserted into or withdrawn from the bone. As described above, the retaining structure 132 of the second bone screw 110 extends about an exterior surface 124 thereof. According to one example, the second bone screw 110 may be a counter-sinkable bone screw including a threading 190 along an entire length of a shaft thereof. The second bone screw 110 may be configured as a substantially headless screw so that, if so desired, the second bone screw 110 may be driven into the bone until a proximal end 111 of the second bone screw 110 is substantially flush with the bone.

A portion of the threading 190 extending along a proximal portion 191 of the second bone screw 110 constitutes the retaining structure 132 engageable via the distal end 122 of the outer shaft 106. As described above, the second hone screw 110 also includes the driving structure 128 extending into the proximal end 111 which, in one embodiment, may be configured as a star or hex-shaped recess, so that when the driving feature 136 of the main body 102 is inserted therein and rotated about the longitudinal axis thereof, the second bone screw 110 may be correspondingly rotated and thereby driven into the hone.

Figure 8:
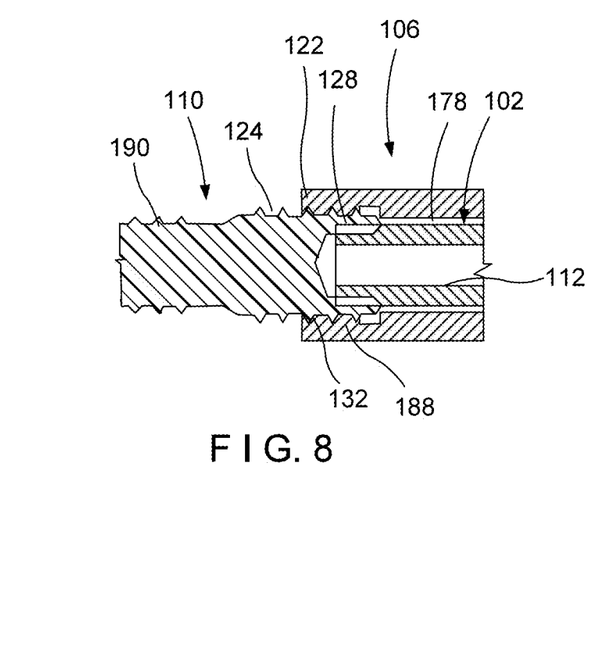
FIG. 8 shows an enlarged longitudinal cross-sectional view of an engagement of the main body and outer shaft with a bone screw, as shown in FIG. 6.

The outer shaft 106 extends from a proximal end 176 to the distal end 122 and includes a channel 178 extending therethrough. The channel 178 of the outer shaft 106 is sized and shaped so that the outer shaft 106 is mountable over the elongated member 112 of the main body 102. The distal end 122 includes a retaining feature 186 configured to engage the retaining structure 132 of the second hone screw 110. In one embodiment, the retaining feature 186 includes a threading 188 extending along the channel 178 at the distal end 122, the threading 188 configured to engage the threading 190 along the proximal portion 191 of the second bone screw 110. Similarly to the elongated member 112 and the longitudinal element 105 of the inner shaft 104, the inner and outer diameters of the proximal portion 180 of the outer shaft 106 are larger than the inner and outer diameters, respectively, of a distal portion 182 thereof. In this embodiment, the inner diameter of the proximal portion 180 corresponds to the outer diameter of the proximal portion 142 of the elongated member 112 of the main body 102 while an inner diameter of the distal portion 182 corresponds to the outer diameter of the distal portion 144.

The proximal portion 180 includes the locking structure 184 mounted therein for engaging the locking recess 156 of the elongated member 112 of the main body 102, when the outer shaft 106 is mounted over the elongated member 112 in a desired position. The locking structure 184 may be configured as a spring loaded element which is biased to project into the channel 178 of the outer shaft 106. As the elongated member 112 is slid distally through the channel 178, the locking structure 184 is pushed radially out of the channel 178 until the locking recess 156 is positioned adjacent to the locking structure 184.

At this point, the locking structure 184 moves radially outward to project into channel 178 to enter the locking recess 156 under its bias. This locks the outer shaft 106 relative to the main body 102 in the desired configuration. In the desired configuration, the outer shaft 106 and the elongated member 112 are positioned longitudinally relative to one another such that the driving feature 136 is positioned within the distal end 122 of the outer shaft 106. Thus, when the assembled main body 102 and outer shaft 106 are connected to the second bone screw 110 to drive the second bone screw 110 into or out of a hone, the driving feature 136 of the main body 102 engages the driving structure 128 of the second bone screw 110 while the threading 188 within the distal end 122 of the outer shaft 106 engages the threading 190 along the proximal portion 191 of the second bone screw 110.

The locking structure 184 and the locking recess 156 engage one another so that the main body 102 is rotatable about the longitudinal axis thereof relative to the outer shaft 106. In one embodiment, the main body 102 and the outer shaft 106 may be rotated to drive the second bone screw 110 into the bone, until the outer shaft 106 is compressed against a surface of the bone. Once the outer shaft 106 is pressed against the bone, the main body 102 may be rotated relative to the outer shaft 106 so that the threading 190 along the proximal portion 191 of the second bone screw 110 engages the bone and is unthreaded from the threading 188 along the interior of the distal end 122 of the outer shaft 102.

A user may rotate the main body 102 while holding the outer shaft 106 at, for example, the locking structure 184, so that the main body 102 may be rotated relative thereto. In one embodiment, a distal end 192 of the proximal portion 180 of the outer shaft 106 is separated from the shoulder 140 of the elongated member 112 of the main body 102 via a distance corresponding to a length of the threading 188 along the interior of the distal end 122 of the outer shaft 106. Thus, when the second bone screw 110 has been driven into the hone such that the proximal end 111 is flush with the bone, the distal end 192 of the proximal portion 180 abuts the shoulder 140 and the threading 190 along the proximal portion of the second bone screw 110 has been entirely unthreaded from the distal end 122. In another embodiment, the main body 102, the outer shaft 106 and the second screw 110 may be configured so that a predetermined number of rotations of the main body 102 relative to the outer shaft 106 will disengage the second screw 110 from the main body 102.

Figure 11:
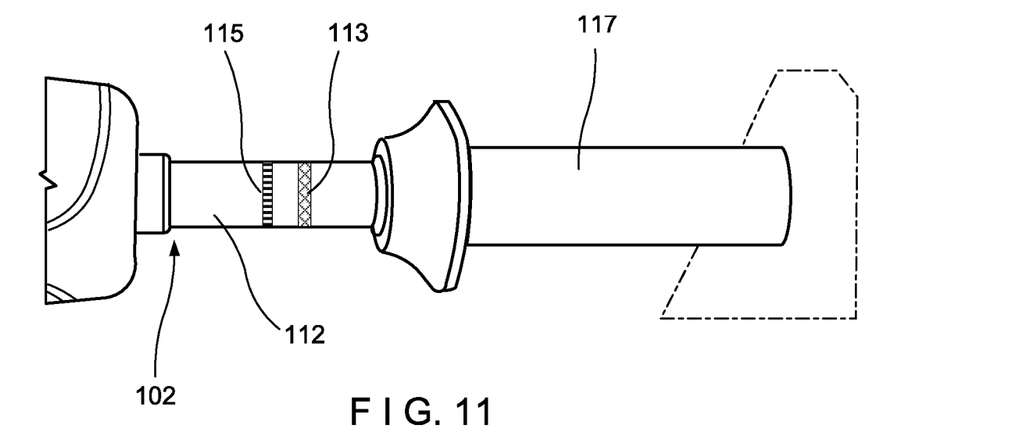
FIG. 11 shows a longitudinal side view of a system according to a further embodiment of the present disclosure.

According to a further embodiment, the main body 102 may include markings along portions of the elongated member 112 to indicate to the user when, for example, either the head 120 of the first bone screw 108 is flush with the bone or when the proximal end 111 of the second bone screw 110 is flush with the bone. The markings may include, for example, lines, etchings and/or grooves. In one example, as shown in FIG. 11, the markings may include lines 113, 115. When the main body 102 is assembled to the inner shaft 104 to drive the first bone screw 108 into the bone, a first one of the lines 113 distal to a second one of the lines 115 may indicate to the user that the head 120 of the first bone screw 108 is flush with the bone when, for example, the first line 113 aligns with a guide sleeve 117 through which it is being inserted. When the main body 102 is assembled with the outer shaft 106 to drive the second bone screw 110 into the bone, an alignment of the second one of the lines 115 with, for example, the guide sleeve 117, will indicate to the user that the proximal end 111 of the second bone screw 110 is flush with a surface of the bone.

Figure 12:
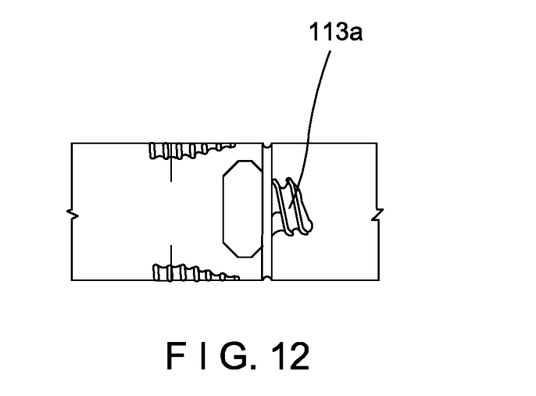
FIG. 12 shows a first longitudinal side view of a system according to another exemplary embodiment of the present disclosure.
Figure 13:
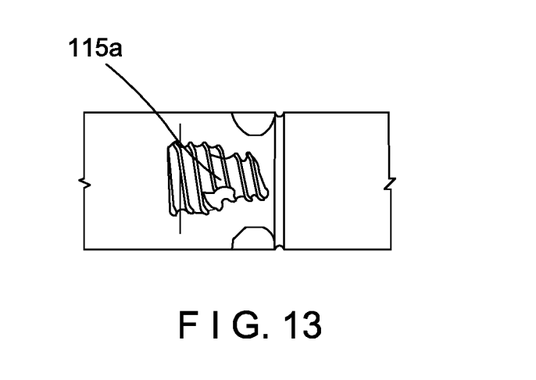
FIG. 13 shows a second longitudinal side of a main body of the system, rotated 90 degrees relative to the first longitudinal side view, according to the system of FIG. 12.

It will be understood by those of skill in the art that the outer shaft 106 may also include a marking (e.g., line) along a portion thereof to show that the second bone screw 110 has been driven into the bone such that the proximal end 111 is flush with an outer surface thereof. In another embodiment, the first and second line markings 113 may also be color coded. According to an even further embodiment, portions of the first and second types of bone screws 108, 110 may be color-coded to correspond to color-coded markings along the main body 102 and/or outer shaft 106 to support ease of use with different screw diameters. In another example, as shown in FIGS. 12-13, markings may also include symbolic etchings 113a, 115a, each symbol corresponding to one of the first and second types of bone screws 108, 110. For example, the symbols may include etchings showing proximal portions of the screws relative to lines or grooves to display to a user when either the head 120 of the first bone screw 108 abuts the bone or when the proximal end 111 of the second bone screw 110 is flush with the bone.

According to an exemplary method utilizing the system 100, a user (e.g., surgeon), selects a type of screw to be used to treat the bone. If the screw selected is a screw such as the first bone screw 108 in which the retaining structure 130 is along the interior of thereof, the user will assemble the main body 102 with the inner shaft 104 by inserting the longitudinal element 105 of the inner shaft 104 through the channel 138 of the elongated member 112 of the main body 102, as shown in FIG. 2. The inner shaft 104 is inserted distally through the channel 138 until the distal end 118 of the inner shaft 104 extends distally from the distal end 116 of the main body 102 so that the distal end 116 may be engaged with the retaining structure 130 of the first bone screw 108. In one embodiment, the inner shaft 104 is rotated about the longitudinal axis thereof in the first direction via the knob 152 so that threading of the retaining feature 154 along the distal end 118 threadedly engages the corresponding threading 149 along the recess 148 of the retaining structure 130.

Upon retention of the first bone screw 108 via the retention feature 154, the distal end 116 of the main body 102 may be inserted into the driving structure 126 within the head portion 120 of the first bone screw 108. As described above, the driving feature 136 at the distal end 116 of the main body 102 and the driving structure 126 of the first bone screw 108 are correspondingly sized and shaped so that the first bone screw 108 may be rotatably driven (e.g., into the bone to be treated) via a rotation of the main body 102 about a longitudinal axis thereof. As the first bone screw 108 is rotatably driven, the first bone screw 108 is prevented from being disengaged from the assembled main body 102 and inner shaft 104 via the retention feature 154. Once the first bone screw 108 has been driven into or out of the bone, as desired, the inner shaft 104 may be disengaged from the bone screw 108 by rotating the inner shaft 104 relative to the first bone screw 108 in the second direction.

If the screw to be used is a screw such as, for example, the second bone screw 110 in which the retaining structure 132 is along the exterior surface 124 thereof, the user assembles the main body 102 with the outer shaft 106 by inserting the elongated member 112 of the main body 102 distally through the channel 178 of the outer shaft 106 until the locking structure 184 of the outer shaft 106 engages the locking groove 156 along the elongated member 112, as shown in FIG. 6. In one embodiment, the distal end 122 of the outer shaft 106 is engaged with the retention structure 132 of the second bone screw 110 prior to locking of the outer shaft 106 with the main body 102 so that, when the locking member 184 is received within the corresponding locking groove 156, the driving feature 136 of the main body is inserted into the corresponding driving structure 128 of the second bone screw 110, which has been retained via the outer shaft 106.

In one embodiment, to retain the second bone screw 110, the outer shaft 106 is rotated relative to the second bone screw 110 so that threading 188 of the retention feature 186 within the distal end 122 engages threading 190 along the exterior surface 124 of the second bone screw 110. As described above, the second bone screw 110 is driven into or out of a bone via rotation of the main body 102 and/or the outer shaft 106 about the longitudinal axis thereof. In particular, main body 102 and the outer shaft 106 are rotated together to drive the second bone screw 110 into the bone until the outer shaft 106 is compressed against a surface of the bone. Once the outer shaft 106 is pressed against the bone, the main body 102 is rotated relative to the outer shaft 106 to drive the proximal portion of the second bone screw 110 into the bone.

As described above, the main body 102 may be selectively assembled with one of the inner and outer shafts 104, 106 based on a type of bone screw to be retained and driven into the bone. The main body 102 may be assembled with and disassembled from the inner and outer shafts 104, 106, as necessary, to insert a variety of different type of bone screws including retention features along an interior or exterior thereof.

Although the second bone screw 110 is shown and described as a substantially headless screw in which the second bone screw 110 may be inserted into the bone such that the proximal end 111 is flush thereto, it will be understood by those of skill in the system 100 may be assembled with one of the inner or outer shafts 104, 106 to drive and retain a variety of different type of bone screws. In another embodiment, for example, a system 200 may be substantially similar to the system 100 described above.

Figure 9:
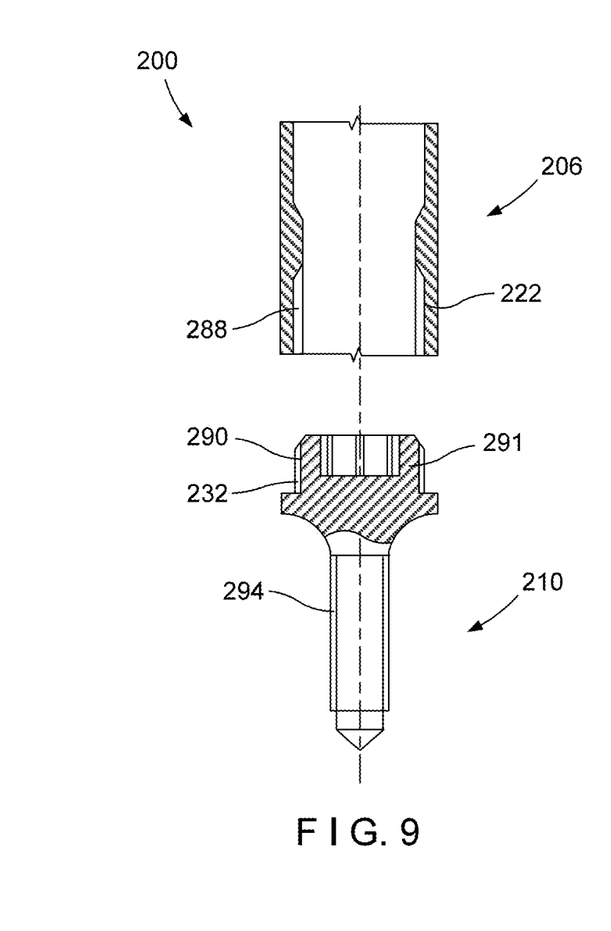
FIG. 9 shows a longitudinal cross-sectional view of a system according to another exemplary embodiment of the present disclosure.

In particular, as shown in FIG. 9, a bone screw 210 of the system 200 may be substantially similar to the second bone screw 110 described above with respect to the system 100, including a retaining structure 232 extending along an exterior of a proximal portion thereof. The bone screw 210, however, may be configured as a standard bone screw including a head portion 291 and a shaft 294 extending distally therefrom. Similarly to the bone screw 110, the retaining structure 232 may include a threading 290 along the head portion 291. Rather than a continuous threading along an entire length thereof, however, the threading 290 along the head portion 291 is separated from a threading extending along the shaft 294 so that the head portion 291 cannot be driven into the bone. Similarly to the second bone screw 110, the threading 290 engages a corresponding threading 288 within a distal end 222 of an outer shaft 206.

Figure 10:
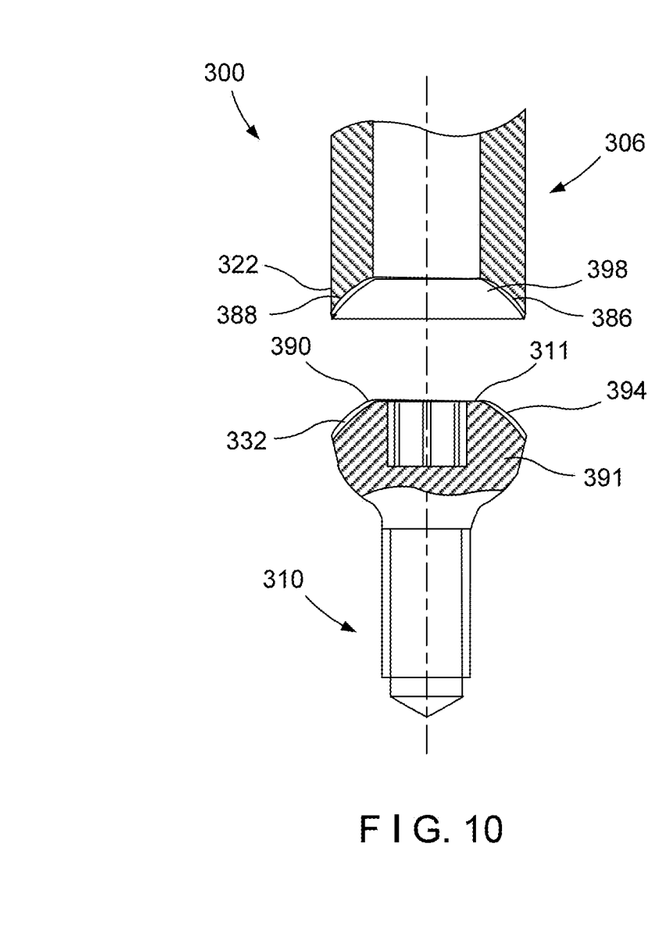
FIG. 10 shows a longitudinal cross-sectional view of a system according to yet another exemplary embodiment of the present disclosure.

According to yet another exemplary embodiment, as shown in FIG. 10, a system 300 may be substantially similar to the systems 100, 200 described above. In particular, a bone screw 310 of the system 300 may be substantially similar to the bone screw 210 described above, including a retaining structure 332 along a head portion 391 thereof. Rather than having a substantially cylindrically shaped head portion, however, the head portion 391 includes a conical proximal portion 394 which tapers toward a proximal end 311 of the bone screw 310 so that threading 390 of the retaining structure 332 extends along this conical portion 394. A distal end 322 of an outer shaft 306, in this embodiment, is correspondingly shaped so that a retaining feature 386 including a threading 388 extends along a correspondingly conically shaped portion 398 at the distal end 322.

It will be understood by those of skill in the art that modifications and variations may be made in the structure and methodology of the present embodiment, without departing from the spirit or the scope of the embodiments. Thus, it is intended that the present embodiments cover the modifications and variations of these embodiments provided that the come within the scope of the appended claims and their equivalents.

What is claimed is:

1. A modular system for treating a bone, comprising:
    a main body including an elongated member extending from a proximal end to a distal end and including a channel extending longitudinally therethrough, the proximal end attached to a handle member and the distal end including a driving feature sized and shaped to engage a corresponding driving structure of one of a first bone screw and a second bone screw;
    an inner shaft including a longitudinal element sized and shaped to be inserted through the channel of the elongated member of the main body, the longitudinal element extending from a proximal end to a distal end including a retaining feature for engaging a corresponding interior retaining structure extending within a recess at a proximal end of the first bone screw; and
    an outer shaft extending longitudinally from a proximal end to a distal end and including a channel extending therethrough, the channel sized and shaped to slidably receive the elongated member of the main body therein and including a retaining feature extending along the distal end thereof, the retaining feature of the outer shaft configured to engage an exterior retaining structure extending along an exterior surface of the second bone screw, wherein the main body is selectively assemblable with one of the inner and outer shaft to drive one of the first and second bone screws into a bone.

2. The system of claim 1, wherein the retaining feature of the inner shaft includes a threading extending along the distal end thereof.

3. The system of claim 1, wherein the inner shaft includes a knob attached to the proximal end of the longitudinal element, the knob extending proximally of the handle member of the main body when the inner shaft is assembled with the main body.

4. The system of claim 3, wherein the knob includes a plurality of grooves along a radially outermost surface thereof to facilitate gripping of the knob.

5. The system of claim 4, wherein each of the plurality of grooves is asymmetrical about a central axis extending through a center of the knob and a midpoint between a first end and a second end of each groove.

6. The system of claim 5, wherein each of the plurality of grooves is configured as a substantially arcuate recess so that a first portion of the arcuate recess extending between the first end and the midpoint has a larger radius of curvature than a second portion of the arcuate recess extending between the second end and the midpoint.

7. The system of claim 1, wherein the retaining feature of the outer shaft includes a threading extending along an interior surface of the channel at the distal end of the outer shaft.

8. The system of claim 1, wherein the outer shaft include a locking member including a tab biased into the channel thereof and the elongated member includes a corresponding locking groove extending about a portion thereof so that, when the elongated member is inserted into the channel of the outer shaft, the tab of the locking member is pushed out of the channel until the locking groove is positioned adjacent the tab and the tab is permitted to revert to its biased configuration to be received within the locking groove.

9. The system of claim 1, wherein the driving structure of the first and second bone screws is configured as a first recess extending into the proximal end thereof, the first recess sized and shaped to correspond to the driving feature of the main body.

10. The system of claim 9, wherein the first and second bone screw further includes a second recess extending distally from the first recess, the retaining structure of the first and second bone screw including a threading extending along the second recess.

11. The system of claim 1, wherein the second bone screw includes a threading extending about an entire length thereof.

* * * * *